US00PP30441P3

(12) United States Plant Patent
Hoogkamp

(10) Patent No.: US PP30,441 P3
(45) Date of Patent: Apr. 23, 2019

(54) ***CURCUMA* PLANT NAMED 'CURGERO'**

(50) Latin Name: *Curcuma alismatifolia*
Varietal Denomination: Curgero

(71) Applicant: Timothy Johan Herman Hoogkamp, Doetinchem (NL)

(72) Inventor: Timothy Johan Herman Hoogkamp, Doetinchem (NL)

(73) Assignee: Nubilus B.V., Naaldwijk (NL)

( * ) Notice: Subject to any disclaimer, the term of this patent is extended or adjusted under 35 U.S.C. 154(b) by 0 days.

(21) Appl. No.: 15/932,757

(22) Filed: Apr. 20, 2018

(65) Prior Publication Data

US 2018/0317364 P1 Nov. 1, 2018

Related U.S. Application Data

(60) Provisional application No. 62/602,663, filed on May 1, 2017.

(51) Int. Cl.
*A01H 5/02* (2018.01)
*A01H 6/00* (2018.01)

(52) U.S. Cl.
USPC ..... Plt./421
CPC ..... *A01H 6/00* (2018.05); *A01H 5/02* (2013.01)

(58) Field of Classification Search
USPC ..... Plt./421
See application file for complete search history.

*Primary Examiner* — Annette H Para
(74) *Attorney, Agent, or Firm* — C. A. Whealy

(57) ABSTRACT

A new and distinct cultivar of *Curcuma* plant named 'Curgero', characterized by its upright and columnar plant habit with outwardly arching leaves; freely clumping growth habit; leaves with dark greyed purple-colored midveins; freely flowering habit; and flowers with light yellow green-colored flower bracts and orange red-colored apices that are positioned just above the foliar plane on strong and erect peduncles.

2 Drawing Sheets

Botanical designation: *Curcuma alismatifolia.*
Cultivar denomination: 'CURGERO'.

BACKGROUND OF THE INVENTION

The present invention relates to a new and distinct cultivar of *Curcuma* plant, botanically known as *Curcuma alismatifolia* and hereinafter referred to by the name 'Curgero'.

The new *Curcuma* plant is a product of a controlled breeding program conducted by the Inventor in Naaldwijk, The Netherlands. The objective of the breeding program is to create new *Curcumas* that have uniform plant habit, good container performance and attractive inflorescence coloration.

The new *Curcuma* plant originated from a cross-pollination made by the Inventor in May, 2011 in Naaldwijk, The Netherlands of a proprietary selection of *Curcuma alismatifolia* identified as code number 20061902-025, not patented, as the female, or seed, parent with a proprietary selection of *Curcuma alismatifolia* identified as code number 20082091-011, not patented, as the male, or pollen, parent. The new *Curcuma* plant was discovered and selected by the Inventor as a single flowering plant within the progeny of the stated cross-pollination in a controlled greenhouse environment in Naaldwijk, The Netherlands in June, 2012.

Asexual reproduction of the new *Curcuma* plant by axillary meristem culture in a controlled environment in Naaldwijk, The Netherlands since February, 2014 has shown that the unique features of this new *Curcuma* plant are stable and reproduced true to type in successive generations of asexual reproduction.

SUMMARY OF THE INVENTION

Plants of the new *Curcuma* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Curgero'. These characteristics in combination distinguish 'Curgero' as a new and distinct *Curcuma* plant:

1. Upright and columnar plant habit with outwardly arching leaves.
2. Freely clumping growth habit.
3. Leaves with dark greyed purple-colored midveins.
4. Freely flowering habit.
5. Flowers with light yellow green-colored flower bracts and orange red-colored apices that are positioned just above the foliar plane on strong and erect peduncles.

Plants of the new *Curcuma* differ from plants of the female parent selection in the following characteristics:

1. Plants of the new *Curcuma* are taller than plants of the female parent selection.
2. Plants of the new *Curcuma* and the female parent selection differ in flower bract color as flower bracts of plants of the female parent selection are white in color.

Plants of the new *Curcuma* differ from plants of the male parent selection in the following characteristics:

1. Plants of the new *Curcuma* and the male parent selection differ in leaf color as plants of the male parent selection have leaves with green-colored midveins.
2. Plants of the new *Curcuma* and the male parent selection differ in flower bract color as plants of the male parent selection have light pink-colored flower bracts.

Plants of the new *Curcuma* can also be compared to plants of *Curcuma alismatifolia* 'Curfroyel', not patented. In side-by-side comparisons plants of the new *Curcuma* differ from plants of 'Curfroyel' in the following characteristics:

1 Plants of the new *Curcuma* are shorter than plants of 'Curfroyel'.
2. Plants of the new *Curcuma* and 'Curfroyel' differ in leaf color as plants of 'Curfroyel' have leaves with green-colored midveins.
3. Plants of the new *Curcuma* have larger flower bract apices than plants of 'Curfroyel'.

BRIEF DESCRIPTION OF THE PHOTOGRAPHS

The accompanying photographs illustrate the overall appearance of the new *Curcuma* showing the colors as true as it is reasonably possible to obtain in colored reproductions of this type. Colors in the photographs may differ slightly from the color values cited in the detailed botanical description which accurately describe the colors of the new *Curcuma* plant.

The photograph on the first sheet is a side perspective view of a typical plant of 'Curgero' grown in a container.

The photograph on the second sheet is a close-up view of a typical inflorescence of 'Curgero'.

DETAILED BOTANICAL DESCRIPTION

The aforementioned photographs and following observations and measurements describe plants grown during the spring and summer in 17-cm containers in a glass-covered greenhouse in Naaldwijk, The Netherlands and under cultural practices typical of commercial *Curcuma* production. During the production of the plants, day temperatures ranged from 22° C. to 28° C., night temperatures ranged from 20° C. to 22° C. and light levels averaged 55 kilolux. Plants were 19 weeks old when the photographs and the detailed description were taken. In the following description, color references are made to The Royal Horticultural Society Colour Chart, 2015 Edition, except where general terms of ordinary dictionary significance are used.

Botanical classification: *Curcuma alismatifolia* 'Curgero'.

Parentage:

*Female, or seed, parent.*—Proprietary selection of *Curcuma alismatifolia* identified as code number 20061902-025, not patented.

*Male, or pollen, parent.*—Proprietary selection of *Curcuma alismatifolia* identified as code number 20082091-011, not patented.

Propagation:

*Type.*—By axillary meristem culture.

*Time to initiate roots.*—About ten days at temperatures about 23° C.

*Time to produce a rooted young plant.*—About 28 to 30 days at temperatures about 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Moderately branching, medium density.

Plant description:

*Plant and growth habit.*—Upright and columnar plant habit with outwardly arching leaves; freely clumping habit with about 17 basal shoots forming per plant; moderately vigorous growth habit.

*Plant height (soil level to top of inflorescences).*—About 55.5 cm.

*Plant diameter.*—About 54.5 cm.

Leaf description:

*Leaf arrangement.*—Alternate; simple.

*Length, fully expanded.*—About 51.4 cm.

*Width, fully expanded.*—About 5.2 cm.

*Shape.*—Narrowly oblanceolate.

*Apex.*—Acuminate.

*Base.*—Sheathing.

*Margin.*—Entire.

*Venation.*—Parallel.

*Aspect.*—Initially upright, then about 45° from vertical.

*Texture and luster, upper and lower surfaces.*—Smooth, glabrous; matte.

*Color.*—Developing leaves, upper and lower surfaces: Close to 143C and 144B. Fully expanded leaves, upper surface: Close to between 137B and NN137D; midvein, close to N186C; secondary venation, close to between 137B and NN137D. Fully expanded leaves, lower surface: Close to NN137D; venation, close to NN137D.

*Leaf sheaths.*—Length: About 14.3 cm. Width: About 1 cm. Height: About 1.2 cm. Texture and luster, upper surface: Smooth, glabrous; moderately glossy. Texture and luster, lower surface: Smooth, glabrous; slightly glossy. Color, upper surface: Close to 143C; at the edges, close to 145B; venation, close to 143A. Color, lower surface: Close to 143A; at the edges, close to 145B; venation, close to 143A.

Inflorescence description:

*Arrangement.*—Dense and upright terminal spike inflorescences developing directly from the basal shoots with numerous showy flower bracts; typically each spike with about nine clusters each with three flowers; about 145 flowers developing per plant.

*Time to flower.*—In The Netherlands, plants flower from spring into autumn; flowering continuous during this period; plants begin flowering about 13 to 17 weeks after planting.

*Flower longevity.*—Flowers last about three days on the plant; flowers not persistent; plants maintain good substance for about 40 days.

*Fragrance.*—Faint; sweet and somewhat spicy.

*Flower buds.*—Length: About 3.3 cm. Diameter: About 9 mm. Shape: Spatulate to oblanceolate. Texture and luster: Smooth, glabrous; glossy. Color: Close to N155A; towards the apex, tinged with close to 90D.

*Inflorescence length.*—About 14.5 cm.

*Inflorescence diameter.*—About 8.5 cm.

*Flowers.*—Length: About 4 cm. Diameter: About 1.6 cm by 2.1 cm. Shape: Zygomorphic with three petals fused towards the base; dorsal petal (labellum) is conspicuous and two smaller lateral petals; calyx with three sepals fused at the base.

*Petals.*—Length, dorsal petal: About 4 cm. Length, lateral petals: About 3.8 cm. Width, dorsal petal: About 1.6 cm. Width, lateral petals: About 8 mm. Shape, dorsal petal: Spatulate with praemorse apex. Shape, lateral petals: Narrowly obovate with obtuse and recurved apex. Texture and luster, all petals, upper surface: Smooth, glabrous; matte. Texture and luster, all petals, lower surface: Smooth, glabrous;

slightly glossy. Color: When opening, dorsal petal, upper surface: Close to N82A fading towards the base to close to N155A; central stripe, close to 17A. When opening, lateral petals, upper surface: Close to NN155D. When opening, dorsal petal, lower surface: Close to 85C to 85D fading towards the base to close to N155A; towards the apex and edges, close to N82A and N82B. When opening, lateral petals, lower surface: Close to NN155D. Fully opened, dorsal petal, upper surface: Close to N82A fading towards the base to close to N155A; towards the margins, close to N82B; central stripe, close to 17A; color becoming closer to N79A fading towards the base to close to 158B to 158D with development. Fully opened, lateral petals, upper surface: Close to NN155D; color becoming closer to 158B to 158D with development. Fully opened, dorsal petal, lower surface: Close to 85C to 85D fading towards the base to close to N155A; towards the apex and edges, close to N82A and N82B; color becoming closer to N79A fading towards the base to close to 158B to 158D with development. Fully opened, lateral petals, lower surface: Close to NN155D; color becoming closer to 158B to 158D with development.

*Sepals.*—Length: About 3.4 cm. Width: About 1 cm. Shape: Narrowly obovate with obtuse and recurved apex. Texture and luster, upper and lower surfaces: Smooth, glabrous; matte. Color: When opening, upper and lower surfaces: Close to NN155D. Fully opened, upper and lower surfaces: Close to NN155D.

*Flower bracts.*—Quantity: About eleven upper bracts and about nine lower bracts per inflorescence. Length, upper bracts: About 7.5 cm. Width, upper bracts: About 4.1 cm. Length, lower bracts: About 3.7 cm. Width, upper bracts: About 4.3 cm. Shape, upper bracts: Ovate. Shape, lower bracts: Broadly obovate; strongly concave. Apex, upper bracts: Acute. Apex, lower bracts: Obtuse. Base, all bracts: Fused. Margin, upper bracts: Entire. Margin, lower bracts: Entire; undulate. Texture and luster, upper bracts, upper and lower surfaces: Smooth, glabrous; slightly glossy. Texture and luster, lower bracts, upper and lower surfaces: Smooth, glabrous; moderately glossy. Color: Upper bracts, upper surface: Close to 145C; towards the apex, strongly tinged with close to 35B to 35C. Lower bracts, upper surface: Close to 146B. Upper bracts, lower surface: Close to 145B; towards the apex, strongly tinged with close to 35B to 35C; main vein, distally, close to 148A. Lower bracts, lower surface: Close to 146B.

*Peduncles.*—Length: About 40.3 cm. Diameter: About 6 mm. Strength: Strong. Texture and luster: Smooth, glabrous; moderately glossy. Angle: Upright, erect. Color: Close to 143A.

*Stamens.*—Quantity: Two per flower. Filament length: About 1.2 cm. Filament diameter: About 3.5 mm. Filament color: Close to NN155D. Anther length: About 5 mm. Anther width: About 1 mm. Anther shape: Narrowly oblong. Anther color: Close to 155A. Pollen amount: Moderate. Pollen color: Close to 155C.

*Pistils.*—Quantity per flower: One. Pistil length: About 3.2 cm. Style length: About 3 cm. Style color: Close to NN155D. Stigma diameter: About 1 mm. Stigma shape: Club-shaped. Stigma color: Close to NN155D. Ovary color: Close to 144C.

*Seeds and fruits.*—Seed and fruit development have not been observed on plants of the new *Curcuma* to date.

Disease & pest resistance: To date, plants of the new *Curcuma* have not been observed to be resistant to pathogens or pests common to *Curcuma*.

Temperature tolerance: Plants of the new *Curcuma* have been observed to be tolerant to temperatures ranging from about 5° C. to about 40° C. and to be suitable for USDA Hardiness Zones 10 to 12.

It is claimed:

1. A new and distinct *Curcuma* plant named 'Curgero' as illustrated and described.

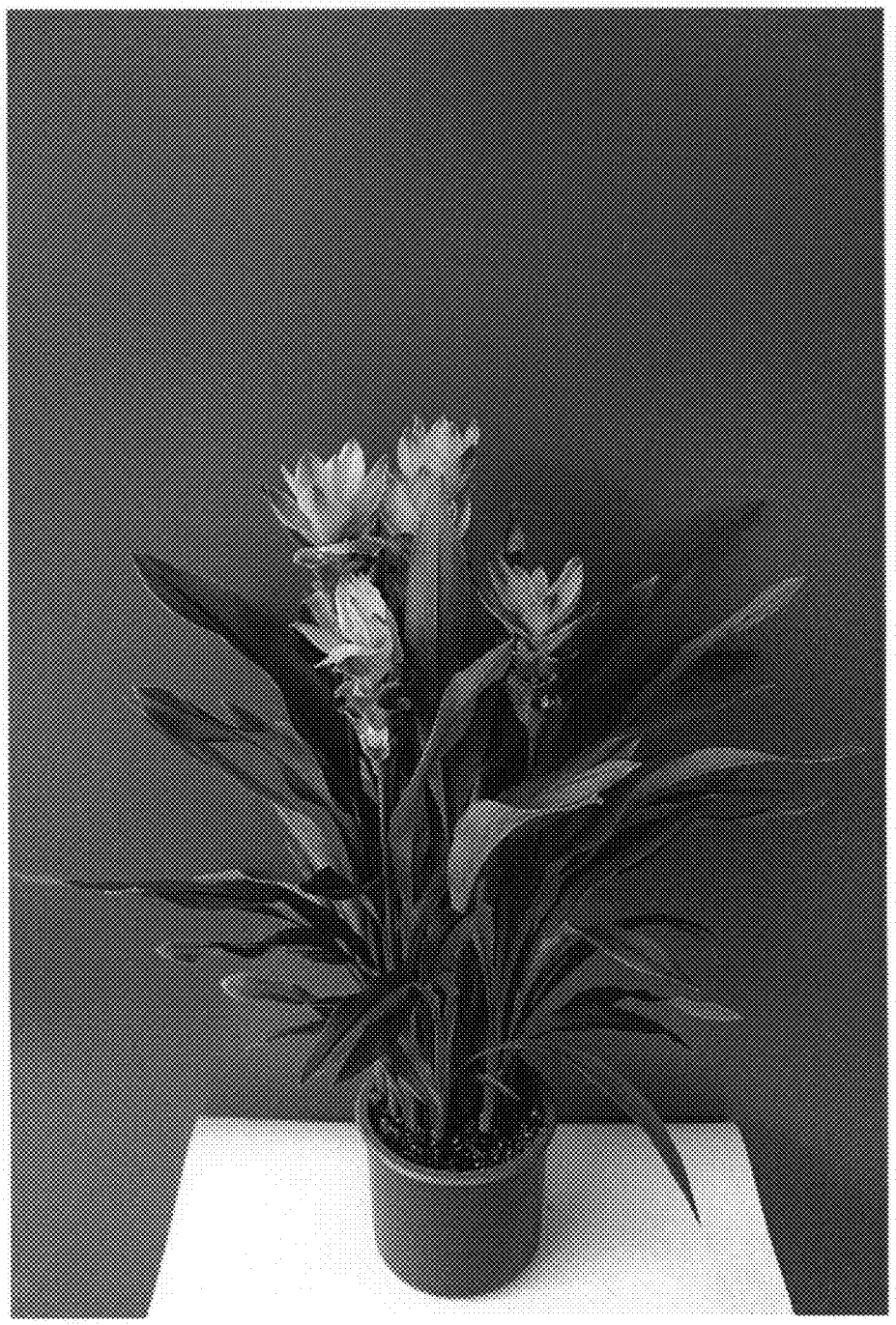

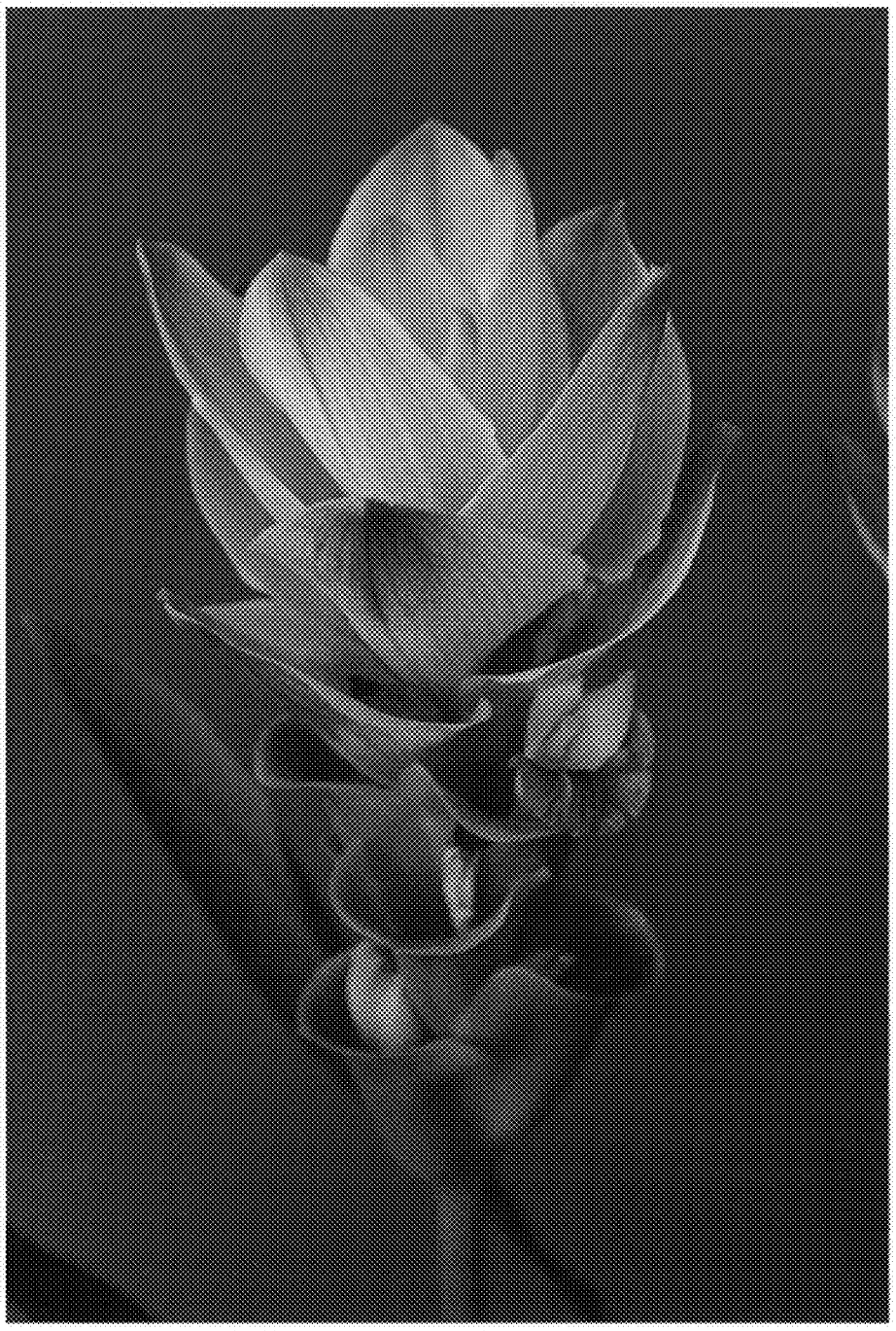

* * * * *